United States Patent [19]

Shoher et al.

[11] Patent Number: 4,826,436
[45] Date of Patent: May 2, 1989

[54] PREFABRICATED DENTAL PROSTHESIS

[76] Inventors: Itzhak Shoher, 50 Shlomo-Hamelech St., Tel-Aviv, Israel, 64386; Aharon E. Whiteman, 13 Il. Perez St., Petach Tikvah, Israel, 49206

[21] Appl. No.: 120,762

[22] Filed: Nov. 13, 1987

Related U.S. Application Data

[63] Continuation of Ser. No. 723,072, Apr. 15, 1985, abandoned.

[51] Int. Cl.[4] ............................................. A61C 13/08
[52] U.S. Cl. .................................... 433/208; 433/167; 433/183
[58] Field of Search ............... 433/208, 183, 222, 218, 433/223, 207, 206, 178

[56] References Cited

U.S. PATENT DOCUMENTS

| | | | |
|---|---|---|---|
| 318,581 | 5/1885 | Sheffield | 433/183 |
| 1,473,661 | 11/1923 | Baker | 433/178 |
| 2,631,373 | 3/1953 | Timm | 433/178 |
| 2,722,053 | 11/1955 | Moyer | 433/178 |
| 3,267,574 | 8/1966 | Oddo | 433/178 |
| 4,059,900 | 11/1977 | Orthwein | 433/178 |

OTHER PUBLICATIONS

The Dental Cosmos, "A New Bridge Denture" 1886, p. 211.

Primary Examiner—Robert Peshock

[57] ABSTRACT

The dental prosthesis of the present invention includes a plurality of flexible metal arm connectors which extend from a common member in forming a bridge or from a common joint in forming a splint. The arm connectors are adapted to be affixed to adjacent retaining members on the abutment teeth to be restored. The arm connectors must be sufficient in length to make reasonable contact with the buccal and lingual surfaces and preferably should contact the occlusal surface as well. The arm connectors may be ring-like in geometry and/or be corrugated for expansion.

5 Claims, 4 Drawing Sheets

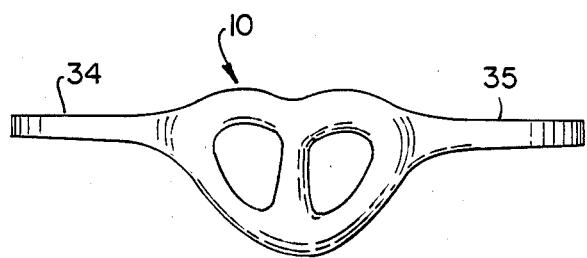
FIG. 3A
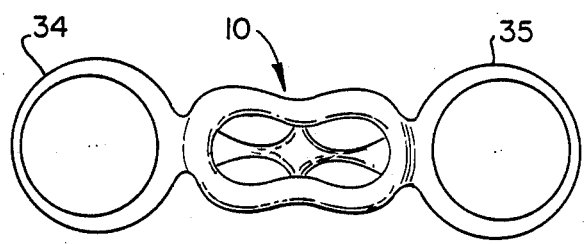
FIG. 3B
FIG. 4A
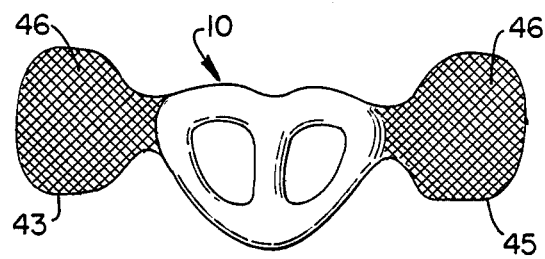
FIG. 4B
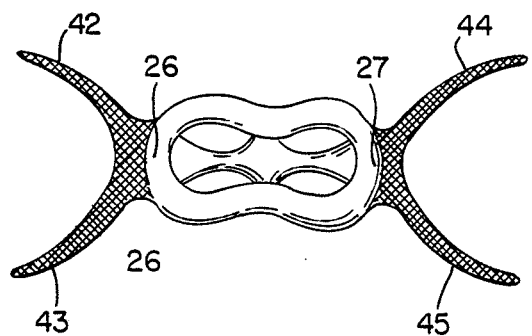

PREFABRICATED DENTAL PROSTHESIS

This application is a continuation of Ser. No. 723,072 filed Apr. 15, 1985, now abandoned.

The present invention relates to a prefabricated dental prosthesis for forming a dental bridge and splint.

BACKGROUND OF INVENTION

Crown and bridge prosthodontics is the science and art of the complete restoration of one or more teeth and the replacement of one or more natural teeth with an artificial device. A bridge is used to replace at least one missing tooth and is supported by natural teeth. The bridge includes a pontic which fills the edentulous space and a soldered joint which serves as a connection between the pontic and a retaining member such as a crown formed on an abutment tooth adjacent the pontic.

The primary purpose of the dental bridge is to receive the forces of occlusion and to transmit them through the abutments so that occlusion is restored to the patient thereby contributing to mastication. The bridge should also augment the ability of the patient to enunciate and maintain the positions of the opposing teeth. The present day construction of a dental bridge is a time consuming, involved and complex process which requires the application of many independent procedures including the following: wasing, spruing, investing, casting, cleaning, trimming, cutting and stoning. The process, as conventionally practiced, is referred to colloquially as the "lost wax casting method" and, at present, is the universally accepted procedure for making a bridge. In following this procedure, each step must be meticulously followed with the dental technician paying strict attention to detail to assure accuracy of the cast product and proper fit. It is not until all of the above steps are completed that the porcelain or other veneering material can be applied and fired to form the finished bridge.

The prefabricated prosthesis of the present invention eliminates waxing and the entire casting operation. Accordingly, there is no waxing, spruing, investing and casting involved nor is cleaning required. The only steps which remain are trimming and grinding and even these steps are limited to the area at the margin. A modified prosthesis of the present invention can also be used in forming a splint for bracing two or more teeth.

SUMMARY OF THE INVENTION

The prosthesis of the present invention for forming a bridge between abutment teeth comprises a first set of a plural number of metal arm connectors represented by thin flexible members having a length sufficient to extend mesiodistally for attachment over at least a portion of the buccal and lingual surfaces of a retaining member mounted on one of the abutment teeth, a second set of a plural number of metal arm connectors for attachment to a retaining member over the opposite abutment tooth and a common member for uniting the first set of arm connectors to the second set of arm connectors. A modified prosthesis of the present invention for forming a splint between abutment teeth comprises a spider arrangement of elongated metal members extending from a common center with the elongated members adapted for attachment to abutment teeth on their lingual, buccal and occlusal surfaces respectively.

Accordingly, it is the principal object of the present invention to provide a prefabricated prosthesis for making a dental bridge or splint.

Other objects and advantages of the present invention will become apparent from the following detailed description of the invention when read in conjunction with the following drawings of which:

FIGS. 3A and 3B represent the side and top view respectively of another embodiment of a prefabricated prosthesis for a posterior tooth in accordance with the present invention;

FIGS. 4A and 4B represent the side and top view respectively of yet another embodiment of a prefabricated prosthesis for a posterior tooth in accordance with the present invention;

DETAILED DESCRIPTION OF THE INVENTION

The prefabricated prosthesis shown in FIGS. 1-7 are alternate embodiments of the present invention. The embodiments of FIGS. 1-5 all show a preformed pontic in a preferred configuration for either a molar or anterior restoration and alternate embodiments of a plurality of arm connectors for attaching the pontic to the retaining members on the abutment teeth. The present invention contemplates the use of any pontic design in combination with any of the arm connector embodiments. In fact, the pontic may be a solid mass and may vary considerably in construction and shape based upon whether a molar or anterior restoration is involved. The prefabricated structures of FIGS. 1-7 may be fabricated from any desired metal or metal composition although the selection of the metal or metal composition should meet the standards of compatibility for use in the oral cavity. Accordingly, a precious or semiprecious metal, metal alloy or composition preferably comprising gold is preferred. In addition, any conventional manufacturing method may be used to fabricate the prosthesis of the present invention including die casting and stamping.

Figure 1A:
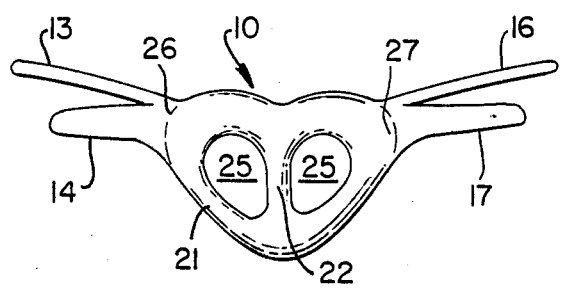
FIGS. 1A and 1B represent the side and top view respectively, of one embodiment of a prefabricated prosthesis for a posterior tooth in accordance with the present invention.
Figure 1B:
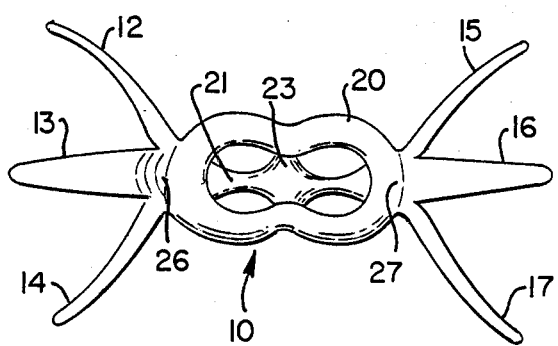

The prosthesis shown in FIGS. 1A and 1B include a pontic 10 and arm connectors 12, 13, 14, 15, 16 and 17 respectively. Although the geometry of the pontic 10 is not critical to the present invention, it is preferred that the pontic 10 be designed having a cradle like shape in accordance with the principles of construction taught and described in U.S. Pat. No. 4,231,740, the disclosure of which is herein incorporated by reference. The pontic 10 includes a plurality of metal members 20, 21, 22 and 23, which interconnect to form a cradle like structure with a large occlusal concavity. The pontic 10 has open spaces 25 between the interconnected members both on the buccal and lingual surfaces which form an open framework. The metal member 21 is looped occluso-cirvically from the interproximal ends 26 and 27 to form an arch. The intermediate members 22 and 23 extend between the members 20 and 21 and function as brace supports. The member 20 is an oval or elliptically shaped member which lies in the occlusal plane between the interproximal ends 26 and 27. The member 20 is depressed to form a surface concavity facing the occlusal surface. Although the design of the pontic 10 should preferably conform to the design criteria taught in U.S. Pat. No. 4,231,740, it is not limited thereto. Any pontic design may be used in conjunction with arm connectors as hereinafter described to form the prosthesis of the present invention.

The pontic 10 has one set of arm connectors 12, 13 and 14, which extend from and form an articulating joint with the interproximal end 26 and another set of arm connectors 15, 16 and 17, which extend from and form an articulating joint with the interproximal end 27. The arm connectors interconnect the pontic 10 to the adjacent abutment teeth to form a conventional three unit bridge. A cantilever bridge may also be formed consisting of a pontic and only one set of arm connectors. A multiple unit bridge may also be formed with two attached pontics and a set of arm connectors extending from the opposite ends of the joined pontics. All of the embodiments of FIGS. 1–5 are examples of a prefabricated prosthesis for a three unit bridge.

Figure 2:
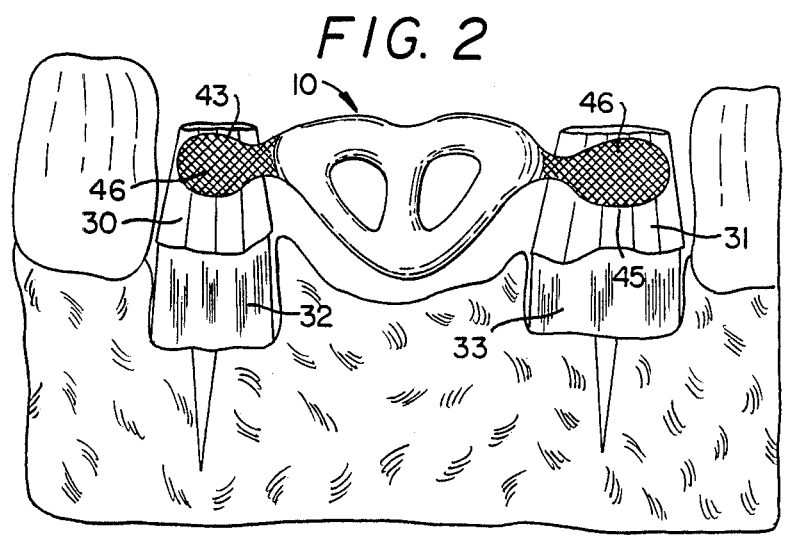
FIG. 2 is a side elevation of the prefabricated prosthesis of FIG. 4 fitted in place upon adjacent copings of abutment teeth in the fabrication of a bridge.

The arm connectors 12, 13, 14, 15, 16 and 17 should be relatively thin, flexible and must be pliable so that they can be adjusted and forced into contact with adjacent retaining members on the abutment teeth independent of alignment between adjacent teeth. FIG. 2 is an example of an arrangement for attaching the prosthesis of the invention to a pair of metal crown copings 30 and 31, in the preparation of a bridge. FIG. 2 uses the arm arrangement of FIG. 4 for illustrative purposes. The metal crown copings 30 and 31 may be fabricated in any conventional manner including casting. It is, however, preferred that the crown copings 30 and 31 be formed following the practice taught in U.S. Pat. No. 4,459,112. In accordance with this patent teaching, the crown copings 30 and 31 would be preformed from metal foils with overlapping folds. The foils are mounted over prepared dies 32 and 33 of the abutment teeth of the bridge and adapted to each die using a conventional swaging device. The adapted crown copings 30 and 31 and the dies 32 and 33 upon which they were adapted are returned to the model as shown in FIG. 2. The preparation of the abutment teeth is not limited to a crown and the present invention is not limited to retaining members in the form of crown copings. Accordingly, the arm connectors of the present invention may be connected to a retaining member on any conventional abutment tooth preparation including a partial crown and a metal inlay.

The arm connectors 12, 13 and 14 of FIG. 1 are intended to be mounted on one adjacent coping so that the arm 12 may be pressed in place over the buccal surface and with the arm 13 pressed against the lingual surface and the arm 14 pressed over the occlusal surface. The length of each arm connector 12, 13 and 14 must be sufficient to cover a reasonable surface area of the buccal, lingual and occlusal surfaces respectively to provide reasonable surface contact. The other set of arm connectors 15, 16 and 17 of FIG. 1 would likewise be pressed in place about the opposite coping in a similar manner. The flexibility an pliability of the arm connectors permit strong attachment to the copings and allow for wide latitude in misalignment. A bond between each of the arm connectors 12–17 and the retainer surface to which it has been physically attached may be formed using any conventional bonding or solder composition. It is, however, preferred to spot weld or spot fuse each arm to the respective coping surface against which the arm has been placed. A fused bond may be formed using a composition of, e.g., finely divided particles comprising 95% Au, 1% Pt, 1% Pd, 1.5% Cu, 1% Ag, and 0.5% AgCl.

Figure 3C:
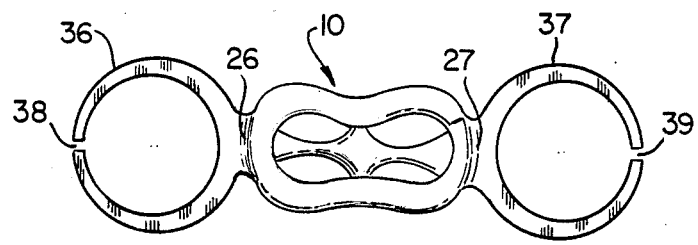
FIG. 3C is a top view of an embodiment similar to FIG. 3B with modified arm connectors
Figure 3D:
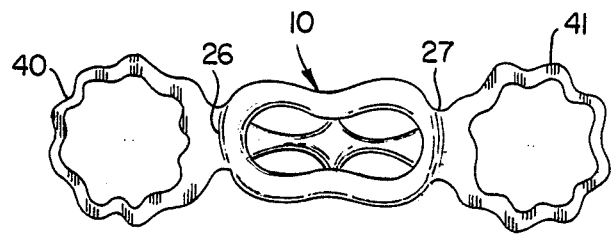
FIG. 3D is another top view of a further embodiment similar to FIG. 3B showing yet another modified arm connector design.

FIGS. 3A and 3B show an alternative three unit prosthesis using the same pontic 10 as shown in FIG. 1. In this embodiment, ring-like arm connectors 34 and 35 are used in place of the corresponding individual arms 12, 14 and 15 and 17 of FIG. 1. Each ring-like arm connector 34 and 35 is slipped over the retaining member on an abutment tooth and bonded or spot welded to the retainer member as described with respect to the attachment of the arm connectors to the copings of FIG. 2. A connector for the occlusal surface although preferred is optional and as such is not shown. The set of arm connectors 12 and 14 and the set of arm connectors 15 and 17 of FIG. 1B may also be replaced with arm connectors as shown in FIGS. 3C and 3D respectively. In FIG. 3C the arm connectors 36 and 37 are ring-like members similar to FIG. 3B except for slitted openings 38 and 39. The slitted openings 38 and 39 permit the arm connectors 36 and 37 to expand to accommodate different size retainer copings. In FIG. 3D the arm connectors 40 and 41 have a rippled or corrugated geometrical shape which permits its expansion to accommodate different size retaining members. In each case a connector for the occlusal surface such as the arm connectors 13 and 16 of FIG. 1B may be used with any of the various alternate arm connector embodiments. The ring-like arm connectors 36, 37 of FIG. 3C and that of FIG. 3D is mounted by slipping it over a corresponding retaining member on an abutment tooth and bonded or spot welded as described heretofore in connection with FIG. 2.

Figure 4C:
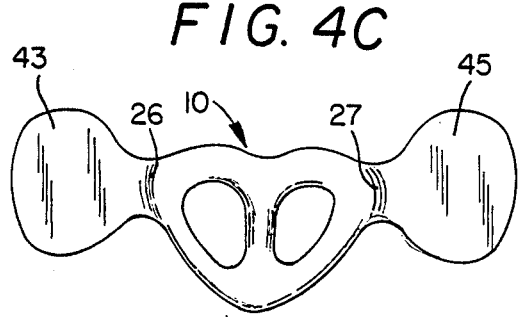
FIG. 4C is a side view of an embodiment similar to FIG. 4A with solid metal arm connectors.

FIGS. 4A and 4B show yet another alternative design for the arm connectors using, for illustrative purposes, the same pontic design 10 as that of FIGS. 1, 2 and 3. In this case, each of the arm connectors 42, 43, 44 and 45, are in the form of a metal mesh with open spaces 45. In this form, the arm connectors 42, 43, 44 and 45 may form a larger surface area than the corresponding connectors of FIGS. 1 and 3, although the amount of metal used in forming the arm connectors of FIG. 4 may be substantially equal to the metal used in forming the connectors of FIGS. 1, 2 and 3. FIG. 4C is an alternative to FIG. 4A in which the same butterfly shape is used for the arm connectors 43 and 45 as indicated in FIG. 4B but of solid metal instead of a metal mesh.

In all of the embodiments of FIGS. 1, 3 and 4, the arm connectors extending from the interproximal ends 26 and 27 of the prosthesis have been shown to be symmetrically compatible with each other. Obviously, for a given situation it may be desirable to use one type of arm connector on one side of the pontic and another type of arm connector on the opposite side or only one set of arm connectors. Again, the arm connector for the occlusal surface is desirable but optional.

Figure 5A:
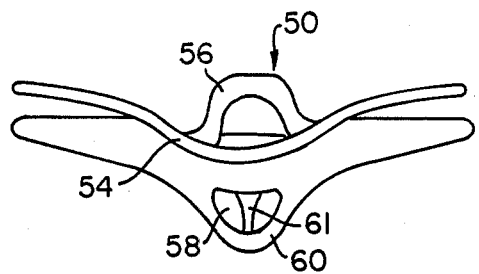
FIGS. 5A and 5B represent a side and top view respectively of a prefabricated prosthesis similar to FIG. 1 with a modified pontic design for forming an anterior bridge.
Figure 5B:
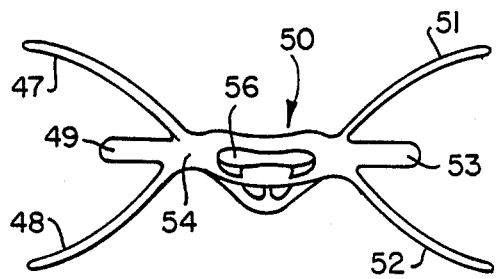

The pontic 10 is preferably used in the construction of a prosthesis for a posterior bridge. FIGS. 5A and 5B show a prosthesis design for an anterior bridge.

The design of the arm connectors 47, 48, 49, 51 52 and 53 are identical to the corresponding arm connectors of FIG. 1 although the configuration of the arm connectors of any of the embodiments in FIGS. 3 or 4 may equally have been used. The design of the pontic 50 in FIGS. 5A and 5B is the preferred pontic design for an anterior tooth in accordance with the teachings of U.S. Pat. No. 4,318,697, the disclosure of which is herein incorporated by reference. The primary difference in the design of pontic 50 from that of pontic 10 is the use of an upper crescent-shaped surface 54 which extends mesial-distally and a metal brace 56 which extends upright from the crescent surface 54 toward the incisal edge of the restoration. The pontic design 50 also provides for open spaces 58 which forms an open framework between the interconnecting metal member 60 and 61 of the pontic 50. The interconnecting members form a central occlusal concavity corresponding to the open space 58.

Figure 6:
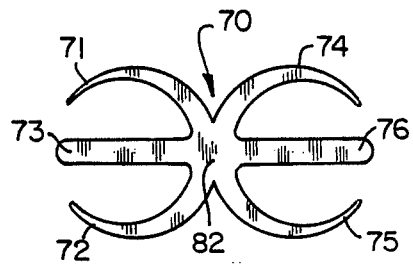
FIG. 6 is a view in elevation of a prefabricated prosthesis in accordance with the present invention for forming a splinted abutment between adjacent teeth.
Figure 7:
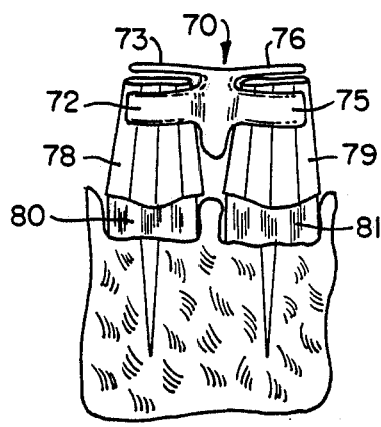
FIG. 7 is a side elevation of the prosthesis of FIG. 6 mounted on the dies of adjacent teeth for forming the splinted abutment.

The prosthesis design of the present invention may also be used to form a splint 70 using a combination of arm connectors without a pontic as shown in FIGS. 6 and 7. The splint 70 may use any of the arm connector arrangements shown in FIGS. 1–5. For simplicity of explanation, the arm connectors 71, 72, 73, 74, 75 and 76 of FIG. 6 have been selected to correspond to the arm connectors 12, 13, 14, 15, 16 and 17 of FIG. 1B and are joined to the retainer copings 78 and 79 of abutting teeth dies 80 and 81 in a manner corresponding to the joining of the arm connectors of FIG. 1B to the crown copings 30 and 31 of FIG. 2. The set of arm connectors 71, 72 and 73 join the set of arm connectors 74, 75 and 76 at the interproximal joint 82 which is seated between the adjacent abutting teeth to be restored. The occlusal arm connectors 73 and 76 are preferred but not essential.

Although the prosthesis of the present invention includes a pontic in combination with arm connectors it is not essential for the arm connectors and pontic to be preassembled as one unit. Thus each set of arm connectors 12, 13, 14 and 15; 16 and 17 may initially be united to each other through a common member such as a metal plate, bar or wires. The common member should preferably be a high fusing temperature metal member so as to reinforce the pontic which will thereafter be formed around it. The common member may either be solid or flexible. Accordingly, each set of arm connectors would be affixed to a corresponding abutment tooth in a manner as heretofore taught with the arm connectors united through the common member which permits self alignment of the connectors through a neutral axis of symmetry extending through the abutment teeth or through a non-symmetrical axis. Thereafter, a pontic of prefabricated design may be attached to the common member or alternatively the pontic may be formed around the common connector using, e.g., the conventional "lost wax" casting method or by using a dental material from which a pontic may be molded and heat treated to form a solid body. The common member should not melt in the furnace during the process of sintering the pontic. Any of the arm connector embodiments of FIGS. 1–5 may be used in combination with the member. Once, however, the pontic is formed, the pontic and common member unite into a single entity relative to each set of arm connectors which extend from the pontic as taught heretofore in forming the prosthesis.

What is claimed is:

1. A prefabricated dental pontic adapted to be joined to at least one metal coping formed from a precious metal foil fixedly mounted upon an adjacent abutment tooth, in the fabrication of a dental bridge without casting, comprising: a metal body having a framework of interconnecting metal members which interconnect to form a cradle-like structure having open spaces between the interconnecting members on both the buccal and lingual sides and at least one arm connector extending mesial-distally from each interproximal end of the pontic with each arm connector having a pliable substantially flat surface for adjustment into physical contact with said metal coping to which it is to be joined by soldering or welding and with the opposite arm connector being independently adjustable to align the pontic between opposing abutment teeth.

2. A prefabricated dental pontic as defined in claim 1 including a pair of arm connectors extending mesial-distally from the interproximal end so as to surround each abutment tooth with the arm connectors of each pair being adjustable and adapted to be joined.

3. A prefabricated dental pontic as defined in claim 2 wherein at least one pair of said arm connectors form a ring-like band joined to the metal retaining member by soldering and/or welding.

4. A prefabricated dental pontic as defined in claim 2 wherein at least one arm connector is in the form of a metal mesh having a multiplicity of open spaces.

5. A prefabricated dental pontic as defined in claim 1 further comprising an arm connector extending occlusally over each metal retaining member.

* * * * *